(12) United States Patent
Christopherson et al.

(10) Patent No.: US 6,805,667 B2
(45) Date of Patent: Oct. 19, 2004

(54) INFORMATION REMOTE MONITOR (IRM) MEDICAL DEVICE

(75) Inventors: Mark A. Christopherson, Shoreview, MN (US); Virginia De La Riva, Minneapolis, MN (US); Gary A. Tapp, Plymouth, MN (US); Andrzej M. Malewicz, Minneapolis, MN (US); Brian P. Schmalz, Minneapolis, MN (US); Troy D. Kopischke, Hamel, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/776,265

(22) Filed: Feb. 2, 2001

(65) Prior Publication Data

US 2002/0045804 A1 Apr. 18, 2002

Related U.S. Application Data

(60) Provisional application No. 60/180,285, filed on Feb. 4, 2000.

(51) Int. Cl.$^7$ .............................. A61B 5/00; A61N 1/18
(52) U.S. Cl. ...................... 600/300; 128/903; 128/904; 607/32
(58) Field of Search ................. 600/300, 301; 128/903, 904; 607/18, 32, 4

(56) References Cited

U.S. PATENT DOCUMENTS

| | | | |
|---|---|---|---|
| 3,769,965 A | 11/1973 | Raddi et al. ........... 128/2.05 R |
| 3,885,552 A | 5/1975 | Kennedy ............... 128/2.05 R |
| 4,142,533 A | 3/1979 | Brownlee et al. ...... 128/419 PT |
| 5,113,869 A | 5/1992 | Nappholz et al. ........... 128/696 |
| 5,345,362 A | 9/1994 | Winkler ....................... 361/681 |
| 5,404,877 A | 4/1995 | Nolan et al. ................. 128/671 |
| 5,467,773 A | 11/1995 | Bergelson et al. ........... 128/709 |
| 5,626,630 A | 5/1997 | Markowitz et al. ........... 607/60 |
| 5,720,770 A | 2/1998 | Nappholz et al. .............. 607/30 |
| 5,749,900 A * | 5/1998 | Schroeppel et al. ........... 607/4 |
| 5,810,735 A | 9/1998 | Halperin et al. ............ 600/486 |
| 5,904,708 A * | 5/1999 | Goedeke ....................... 607/18 |
| 5,944,659 A | 8/1999 | Flach et al. ................. 600/300 |
| 6,073,046 A | 6/2000 | Patel et al. .................. 600/509 |
| 6,152,885 A | 11/2000 | Taepke ........................ 600/561 |
| 6,162,180 A | 12/2000 | Miesel et al. ................ 600/481 |
| 6,190,326 B1 * | 2/2001 | McKinnon et al. .......... 600/300 |
| 6,238,338 B1 * | 5/2001 | DeLuca et al. ............... 128/903 |
| 6,250,309 B1 * | 6/2001 | Krichen et al. .............. 600/300 |
| 6,416,471 B1 * | 7/2002 | Kumar et al. ................ 128/903 |

* cited by examiner

Primary Examiner—Mary Beth Jones
Assistant Examiner—Michael Astorino
(74) Attorney, Agent, or Firm—Michael C. Soldner; Girma Wolde-Michael (57) ABSTRACT

An information remote monitor (IRM) is implemented to collect medical device data locally in a patient's home for transmission to a remote location. Specifically, the IRM integrates data from an external pressure reference (EPR) and an implanted medical device (IMD), preferably the Chronicle™, for remote transmission to a server or a clinical center for follow-up, monitoring and evaluation. The IRM utilizes wireless telemetry to downlink to the IMO and directly engages the EPR to download barometric pressure data to correct cardiac pressure readings from the Chronicle™ or IMO. The IRM may be connected serially to a PC and the PC may control the functions of the IRM. In the alternate, the PC may be used to transfer data from the IRM, through a Web-enabled network system, to a server or a remote location. The IRM utilizes an integral modem to dial a server and transfer patient data via FTP, PPP and TC/PIP protocols. The IRM includes ergonomic shapes and features adapted for home use including a highly simplified and illustrative user interface that enables the patient to easily operate the device to successfully transfer medical data as needed.

15 Claims, 9 Drawing Sheets

INFORMATION REMOTE MONITOR (IRM) MEDICAL DEVICE

This application claims priority to Provisional Patent Application No. 60/180,285 filed Feb. 4, 2000, and incorporates the specification and drawings in their entireties by reference herein.

FIELD OF THE INVENTION

The present invention generally relates to medical devices. Specifically, the invention relates to an interface device implemented to telemetrically and wirelessly transmit physiologic and cardiac data obtained from one or more implantable medical devices (IMDs). More specifically, the invention relates to an information remote monitor (IRM) medical device, having data communications with the IMDs and a remote computer/server that is accessible by Medtronic, Inc. and other care providers to seamlessly and continuously transfer data and enable remote monitoring and management of patients with chronic disease. Preferably, the IRM is placed in the patient's home/room to access the IMD and transmit stored data via various data transmission schemes to a remote server or other expert centers.

BACKGROUND OF THE INVENTION

The present invention relates generally to telemetry systems for uplink and downlink telemetry transmission between at least one implantable medical device and an IRM. The IRM is implemented to overcome the problems encountered in providing patient services that are generally limited to in-hospital operations.

Prior art methods of reviewing patient data and conducting clinical follow-ups on patients with one or more IMDs, requires a patient to go to a clinic or hospital. Further, if the medical condition of a patient with an IMD warrants a continuous monitoring or adjustment of the device, the patient would have to stay in a hospital indefinitely. Such a continued treatment plan poses both economic and social problems. Under the exemplary scenario, as a segment of the population with IMDs increases, many more hospitals/clinics, inlcuding service personnel will be needed to provide in-hospital service for the patients, thus escalating the cost of health care. Additionally, the patients would be unduly restricted and inconvenienced by the need to either stay in the hospital or make very frequent visits to a clinic.

Yet another condition of the prior art practice requires that a patient visit a clinic center for occasional retrieval of data from the IMD to assess the operation of the device and gather patient history for both clinical and research purposes. Further, if a patient with IMDs is taking a drug, it is often clinically prudent to monitor the dose and its impact on the performance of the IMD. Furthermore, the IMD may be adapted to monitor the patient's drug intake, compliance and effectiveness by directly measuring the dose of the drug in the patient. Normally, such data is acquired by having the patient in a hospital/clinic to download the stored data from the IMD or by direct examination, such as, for example, a blood test. Depending on the frequency of data collection, this procedure of assessing a chronic condition of a patient with IMDs may pose serious difficulty and inconvenience for patients who live in rural areas or have limited mobility.

Current practice in the art involves the use of an external programming unit for non-invasive communication with IMDs via uplink and downlink communication channels associated with the programmers. In accordance with conventional medical device programming systems, a programming head is used for facilitating two-way communication between IMDs and the programmer. In many known implanted IMD systems, a programming head is positioned on the patients body over the IMD side such that one or more antennae within the head can send RF signals to, and receive RF signals from, an antenna disposed within the hermetic enclosure of the IMD or disposed within the connector block of the IMD in accordance with common practice in the art. As was indicated hereinabove, procedures that require downlink and uplink using programmers require that the patient be present at the hospital or clinic. A programmer of this type is described in more detail in U.S. Pat. No. 5,345,362 issued to Thomas J. Winkler, entitled PORTABLE COMPUTER APPARATUS WITH ARTICULATING DISPLAY PANEL, which patent is hereby incorporated herein by reference in its entirety.

In the context of the present invention, programmers are complicated and expensive units to deploy in patients' homes to implement a highly distributive chronic patient monitoring and management. Notwithstanding, more recently, it has been proposed to provide communication systems for IMDs in which the programming head is eliminated and communication occurs directly between the IMDs and the programmer located some distance from the patient. Such programmers still require the patient to be within telemetry range and therefore are not compatible with a remote patient management. Such systems are disclosed in U.S. Pat. No. 5,404,877 to Nolan et al, and U.S. Pat. No. 5,113,869 to Nappholz. In the Nappholz patent, in particular, broadcasting RF signals from an IMD to a programmer that may be located some feet away from the patient, is suggested. Such a communication system is also disclosed in U.S. patent application Ser. No. 09/303,178 for A TELEMETRY SYSTEM FOR IMPLANTABLE MEDICAL DEVICES, filed Apr. 30, 1999 by Villaseca et al, which application is incorporated herein by reference in its entirety.

In the context of remote communication relating to IMD data transfer and exchange, for example, U.S. Pat. No. 3,769,965 issued to Raddi et al, discloses a monitor apparatus for implanted pulse generator. Specifically, a monitor apparatus is disclosed for monitoring electrical stimulation signals due to either natural or artificial electrical stimulation of a body part via a communication link such that the repetition rate of the electrical stimulation signals can be determined. The monitor apparatus comprises the subsystems: a transducer; a communication link or network; and a receiver. The transducer is adapted to sense the electrical stimulation signals generated either naturally or by an electronic organ stimulator, such as an implanted cardiac pacer, and to convert the electrical stimulation signals to audible signals such as tone bursts. These audible tone bursts are then transmitted over a communication link such as the standard telephone network to the receiver located at a remote telephone station, typically a cardiologist's office. The receiver is adapted to measure the time interval between received tone bursts. The receiver is further adapted to display or indicate to an observer the time interval between received tone burst. If desired, the receiver can be adapted to indicate directly the repetition rate of the stimulation signals. The information is then utilized by an observer for diagnostic purposes. The monitor apparatus also includes a test means for testing the integrity of the apparatus including the transducer, the communication link and the receiver.

Further, U.S. Pat. No. 3,885,552 issued to Kennedy discloses a diagnostic method and system for the detection and transmission of data from a remote location to a central location.

U.S. Pat. No. 4,142,533 issued to Brownlee et al, discloses a monitoring system for cardiac pacers. It discloses a complete system for telemetering and monitoring the functioning of an implanted pacemaker as well as controlling the testing of the functions from a remotely located central facility is disclosed specifically comprising the provision of capabilities for directly and simultaneously transmitting from the pacer, electrical signals indicative of multiple pacer functions, such as, pacer rate, cell voltage, refractory period, heart rate with pacer inhibited, R-wave level and sensing margin, sensing circuit and other component failure, cardiac electrode lead break, and hermetic integrity. The indicative signals are picked up at the patient's location for local analysis and/or telephonically communicated to a remote central monitoring station. The central station may control testing of the pacemaker functions by transmitting command signals back telephonically for coupling through cooperating external and implanted inductances or magnetically controlled switches to the implanted pacer circuitry. U.S. Pat. No. 5,467,773 issued to Bergelson et al, discloses cardiac pacing remote monitoring system. Remote monitoring of cardiac electrical activity and/or pacemaker function under extensive control by personnel at a central station over the operation of a monitoring instrument at the patient's home, to thereby reduce reliance on active participation by the patient and to enhance useful information and suppress undesirable information in the signals transmitted between the home monitoring unit and the central station. U.S. Pat. No. 5,626,630 to Markowitz et al, discloses a medical telemetry system using an implanted passive transponder. The telemetry system includes a remote monitoring station, a repeater worn externally by a patient and a quasipassive transponder attached to a device implanted in the patient. The remote monitoring station communicates to the repeater to initiate an interrogation routine between the repeater and the transponder to extract patient condition information from the implanted device. When the repeater receives the condition information, it relays it to the remote monitoring station. The transponder is specially designed to operate with an extremely low level of power, less than 1 nW/baud, and to be compatible for attachment to existing implanted devices. The transponder can operate at a very high data rate, including a rate of about 100 kbps. U.S. Pat. No. 5,720,770 to Nappholz et al, discloses a cardiac stimulation system with enhanced communication and control capability. Specifically, a cardiac stimulation system is provided which delivers long term cardiac therapy without a personal supervision by a physician. The system includes a cardiac stimulation device implanted in a patient and an external device in constant or periodic communication with the cardiac device. The external device is used to control the pacemaker operation. The external device receives updates of the condition of the patient and the operation of the cardiac device and the therapy provided by the cardiac device. This information is transmitted by the external device over a standard telephone network which may consist of hardwired network, a cellular network, or a combination thereof to a remote control device operating near the physician and/or a monitoring station used for monitoring and data logging information from a plurality of patients. The cardiac device, through the external device can also communicate directly and exchange information with the patient over an RF channel. Finally, the external device may be provided with ground position indication system for locating the patient geographically in an emergency. U.S. Pat. No. 5,944,659 to Flach et al, relates to architecture for TDMA medical telemetry system. A medical telemetry system is provided for collecting the real-time physiologic data of patients (including ambulatory patients) of a medical facility, and for transferring the data via RF to a real-time data distribution network for monitoring and display. The system includes battery-powered remote telemeters which attach to respective patients, and which collect and transmit (in data packets) the physiologic data of the patients. The remote telemeters communicate bi-directionally with a number of ceiling-mounted RF transceivers, referred to as "VCELLs," using a wireless TDMA protocol. The VCELLs, which are hardwire-connected to a LAN, forward the data packets received from the telemeters to patient monitoring stations on the LAN. The VCELLs are distributed throughout the medical facility such that different VCELLs provide coverage for different patient areas. As part of the wireless TDMA protocol, the remote telemeters continuously assess the quality of the RF links offered by different nearby VCELLs (by scanning the frequencies on which different VCELLs operate), and connect to those VCELLs which offer the best link conditions. To provide a high degree of protection against multi-path interference, each remote telemeter maintains connections with two different VCELLs at-a-time, and transmits all data packets (on different frequencies and during different timeslots) to both VCELLs; the system thereby provides space, time and frequency diversity on wireless data packet transfers from the telemeters. The telemeters and VCELLs also implement a patient location protocol for enabling the monitoring of the locations of individual patients. The architecture can accommodate a large number of patients (e.g., 500 or more) while operating within the transmission power limits of the VHF medical telemetry band. U.S. Pat. No. 6,073,046 issued to Pattel et al, discloses a heart monitor system to enable a medical facility, after discharge of a cardiovascular patient, to remain in contact with the patient. The patient is provided with a multiple lead EKG terminal spread placed on the body, and the signals therefrom are collected and transmitted. They are transmitted to a remote central location. At the central location, the transmitted EKG data is analyzed. It is compared with normal EKG signals and signals captured in time from the same patient as part of the patient history. The evaluation is done through a neural network which forms an output signal automatically or through intervention of a cardiologist sending an alarm condition signal to the patient instructing the patient to get immediate treatment at the patient's location or to otherwise go to a specific medical facility. Signal preparation includes providing EKG signals through a multiplexer, conversation into a digital data, removal of bias signals, stabilization of this EKG base line, compression and data transmission through a modulator. The receive signal is reconstructed to provide an EKG signal of the patient which is then evaluated in the neural network. As appropriate, transmitter/receiver repeater stations and synchronous satellites are used to convey these signals. U.S. Pat. No. 6,162,180 issued to Miesel et al discloses a non-invasive cardiac monitoring system and method with communications interface. Specifically, a system and method for determining a patient's cardiac output in a non-invasive manner and transmitting cardiac output data to a remote host processor, a communications system, or a local output device is disclosed. A noninvasive cardiac monitoring approach utilizes an implantable medical device coupled to an oxygen sensor. The oxygen sensor provides venous oxygen saturation data to the implantable medical device. An oxygen consumption unit produces oxygen consumption data using air exhaled by a patient. A processing unit calculates a cardiac output result in real-time using the venous oxygen saturation data, the oxygen consumption data, and arterial oxygen saturation data assumed to be about 100% or acquired using a sensor external to the patient. The implantable medical device may transmit the venous oxygen saturation data to the processing unit using electromagnetic signals or acoustic signals. The implantable medical device may be a pacemaker, a pacemaker, cardioverter, defibrillator (PCD), an oxygen sensing device, or an implantable hemodynamic monitor. The processing unit may store the cardiac output data/result for a period of time and/or communicate the cardiac output result to the remote host processor substantially in real-time via a communications interface. The interface may include a modem, a computer interface, a network interface, or a communications system interface, for example. The processing unit may communicate the cardiac output result to the remote host processor in an analog, digital or optical form.

Use of the systems of the prior art may not be conducive for patients to stay in their home while receiving a high quality continuous monitoring and clinical service. In sharp contrast, the IRM of the present invention is intended to provide means for a patient to transmit data from their residence to a health care provider and/or remote server. As will be discussed in the preferred embodiments herein, the design is focused on making the process very easy and automated for the patient. The complete system of the IRM in conjunction with a server, a web browser and a remote communication system, allows the patient to stay in their home, thus reducing patient visits to the physician or the hospital, while increasing the level of care at a reduced cost.

SUMMARY OF THE INVENTION

The present invention relates to a communications system between one or more implanted devices (IMDs) in a patient and an associated information remote monitor (IRM) located at a distance from the IMDs to enable the transmission of physiologic and cardiac data from at least one of the IMDs.

In a preferred embodiment the IRM includes software adapted to communicate with Chronicle® which is an implantable hemodynamic monitor. The Chronicle® without limitation, stores trend data in a large buffer in RAM with resolution ranges from a few seconds to several minutes, depending on storage time interval.

The IRM is implemented to collect patient/medical device data in a patient's home for transmission to a remote server or clinician to enable remote and chronic patient monitoring and management. In the preferred embodiment the IRM is adapted to download data from an external pressure reference (EPR) simultaneous with downloading data from the Chronicle® using a wireless telemetry data transfer.

The IRM is adapted for connection to a PC to use the PC for data transfer. In the alternate, the PC may be used to control the IRM and program the implanted device thereby implementing the IRM as a programmer. In the context of the present invention, the IRM could transfer EPR and Chronicle® (IMD) data through the PC to a server or a remote clinical/physician center. The IRM may also, via a modem and other wireless communications media, transfer the data to a server or the remote center. In one embodiment, the IRM utilizes an integral modem to dial a server and transfer data via FTP, PPP and TC/PIP protocols.

The IRM includes various structures to promote ease of use in the home environment. Specifically, ergonomic structures in combination with user interface instructions, displays and audible communication make the IRM a user friendly device for application in the home environment.

DETAILED DESCRIPTION OF THE PREFERRED EMBODIMENTS OF THE INVENTION

The present invention relates to the transmission of physiologic and cardiac data obtained from preferably a Chronicle® implantable heart monitor to a remote computer or server that is accessible by Medtronic and other care providers. The data transmitted from a patient's home or room via transmission methods such as cellular phone links, LANS, RF links, regular phone lines, cable modems and the like. The IRM is ergonomically designed for home use and includes a highly simplified but effective user interface to enable the patient to use the device without assistance from others.

Although the IRM includes software that is adaptable to communicate with various types of IMDs, including but not limited to neural implants, drug delivery systems and other medical devices, for the purposes of this disclosure, the Chronicle® is considered the IMD with which data communication and transmission are effectuated. Chronicle® is a hemodynamic monitor and includes circuitry for data storage, recovering and processing of pressure, electrogram, heart rate, core temperature, and activity data. Triggered events cause high resolution data collection that is beat to beat for approximately 18 minutes before and after 6 minutes post event. There are three types of triggers, including bradycardia trigger, tachycardia trigger, and patient activated trigger. The bradycardia trigger and tachycardia trigger are automatic, and the patient activated trigger requires the application of the antenna by placing it at the IMD's position in the patient's body. In the alternate, a wireless communication may be implemented using, for example, various types of RF signals blue tooth or equivalent.

Generally, a communication between the IMD and the IRM could be via direct antenna placement or telemetrically within a range of a few feet. The IMD may employ, for example, an elongated antenna which projects outward from the housing of the IMD as described in the cited Villaseca et al application, or may employ a coil antenna located external the housing.

Figure 1:
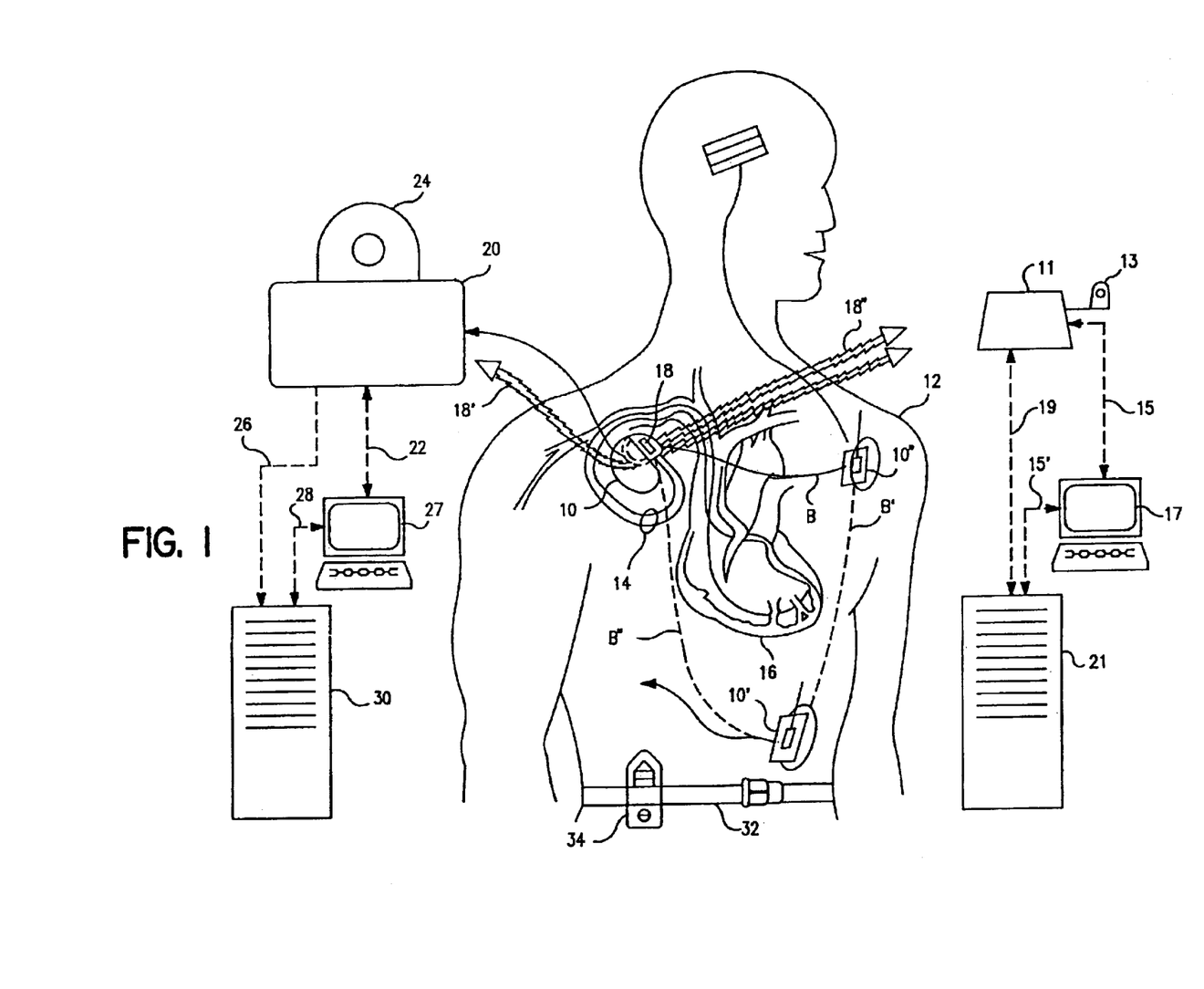
FIG. 1 shows a diagram illustrating a program and the IRM to the present invention, communicating with one or more implantable medical devices (IMDs) in a patient.

FIG. 1 is a simplified schematic diagram representation of a functional uplink and downlink bi-directional communication in accordance with the present invention. Specifically, one or more IMDs such as IMD 10, 10' and 10" may be implanted in patient 12. It may also be possible for the IMDs to have internal communications, B, B' and B". The IMDs may consist of cardiac device 10, drug delivery device 10', neurological drug device 10" and many others as may be needed to provide the necessary therapy, diagnosis and clinical care to patient 12.

IMD 10 is also shown to have wireless communication with programmer 11 via wireless telemetry line 18". As was discussed hereinabove, any downlink and uplink operations that implement programmer 11 would require the patient to go to the hospital or clinic. This is particularly because programmer 11 is rather robust. Programmer 11 is also expensive and technically complicated to operate, and is not easily adaptable for in-home use by patients.

However, the present invention provides tailored services that parallel some of the operations of programmer 11 at reduced cost and in user friendly settings For example, programmer 11, after an uplink or downlink could communicate via communication lines 15 with PC 17 or with a Medtronic server 21 via link 19. Communication lines 15 and 19 represent, without limitation, a modem, an ISDN line, cable, RF, telephone line and may also represent a secure intranet, internet, extranet or World-Wide Web environments to enable data transmission between programmer 11, PC 17 and server/computer 21. Further, using similar data transmission systems, PC 17 which is in bi-directional data communication with server 21 would enable access to stored data and can transfer information between them. One aspect of the uplink and downlink operation, using programmer 11, requires either a physician or a technician to be able to operate programmer 11. External pressure reference EPR13 measures and records barometric pressure which is necessary for correlation to atmospheric pressure. The Chronicle® is generally used in patients with chronic CHF, undergoing serial clinical management. It is generally used to complement existing CHF therapies and disease management regimens in order to provide precise therapy management, early intervention by remote monitoring of impending decompensation and to improve quality of life. In this regard, the use of programmer 11 outside the hospital or clinic environment becomes highly impractical.

Referring now to the left side of FIG. 1, IRM 20 is shown in data communications with IMD 10. IMD 10 is implanted in patient 12 beneath the patient's skin or muscle, and is electrically coupled to heart 16 of patient 12 through pace/sense electrodes and lead conductors, or at least one cardiac pacing lead 14 in a manner known in the art. IMD 10 may represent Chronicle® which contains an operating system that may employ a microcomputer or a digital state machine for timing, sensing, data storage, recovery and processing of pressure, electrogram, heart rate and other related data, to thereby monitor the hemodynamic environment.

IRM 20 includes telemetry hardware and software which implement an automatic gain control, for instance AGC algorithm to a low, easier positioning of antenna 18 by patient 12. In an alternate embodiment, a wireless communication line 18' could also be implemented. For the purposes of the present invention, the placement of antenna 18 by the patient on IMD 10, without limitation, is considered the preferred procedure to trigger data transfer or uplink.

IRM 20 includes ergonomic features that make it highly compatible for in-home use by a patient. For example, the upright shape of IRM 20 enables the unit to sit on a counter or on a nightstand. Further, the user interface, including a start button, are located in positions which make them highly accessible to the patient. As will be discussed hereinbelow, various aspects of the design of IRM 20 make it highly adaptable for home use. Further, IRM 20 and EPR 24 are adapted to transfer time stamped long term barometric pressure data to enable correction of cardiac pressure readings due to barometric pressure uplinked from Chronicle®, (IMD 10) to IRM 20.

EPR 24 is generally carried by patient 12 or a belt implement 32 or is kept in close proximity to patient 12. EPR 24 is used to derive reference pressure data for use in combination with absolute pressure derived from Chronicle® (IMD 10). Various embodiments of this device are disclosed in U.S. Pat. No. 6,152,885 issued to Taepke, which patent is incorporated herein by reference in its entirety. Similarly, U.S. Pat. No. 5,810,735 to Halperin et al, discloses external patient reference sensors of internal sensors.

Figure 2:
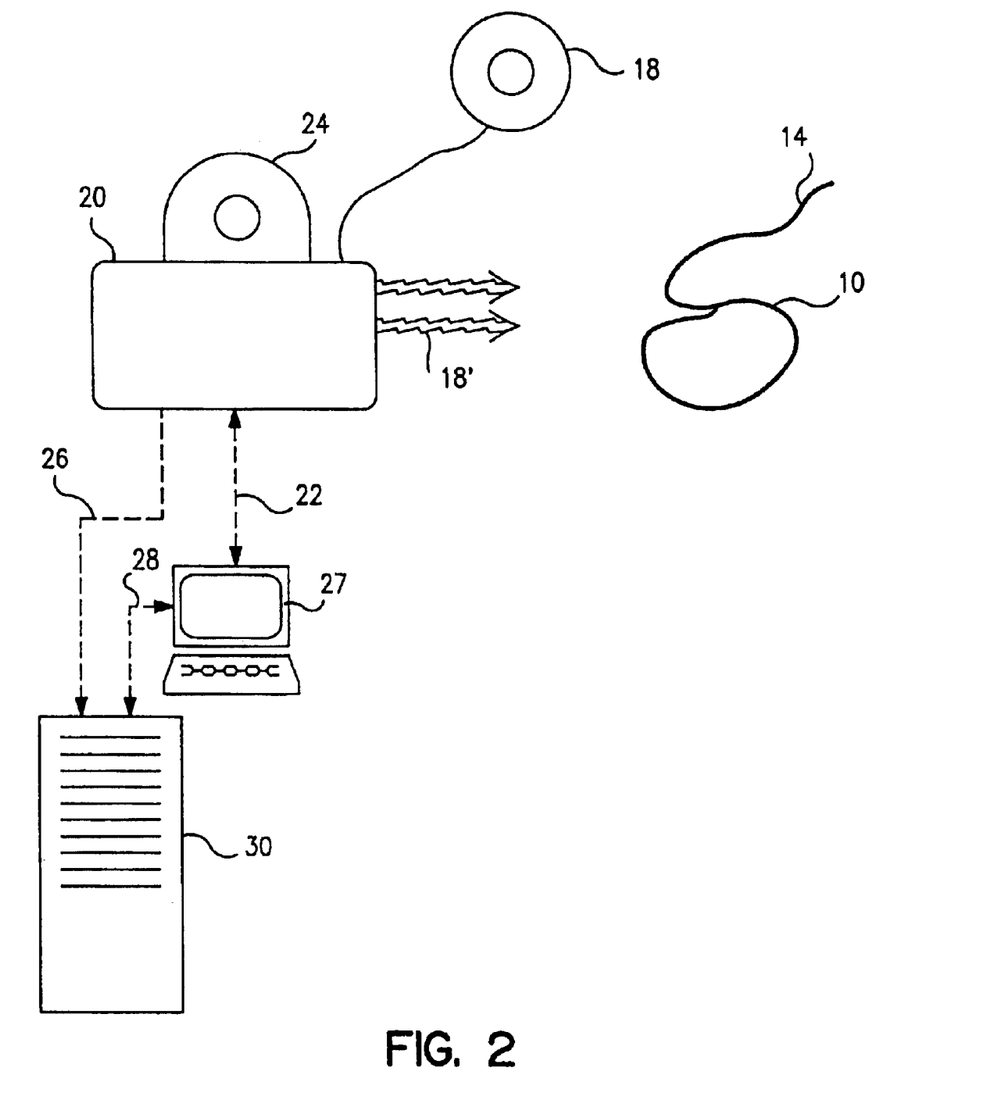
FIG. 2 represents the IRM of the present invention in telemetry communications with an IMD such as the Chronicle® and a data transmission scheme.

Referring to FIG. 2, IRM 20 is shown in telemetry communication with Chronicle® IMD 10. Generally, cardiac data is transmitted to IMD 10 via lead 14 as described hereinabove. During an uplink or a downlink session, telemetry communication is established between IMD 10 and IRM 20. Communication could be via antenna 18 or wireless communication such as RF signals 18' as is discussed hereinbelow. Patient 12 triggers an uplink session by installing EPR 24 in a designated slot and push the start button. The microcontroller in IRM 20 will look for EPR 24 and if it confirms the existence of EPR 24 it will start downloading barometer data into IRM 20. Thereafter, telemetry is enabled and data will start being transmitted from IMD 10. When all the data from IMD 10 is telemetered down, then IRM 20 will try to transmit the data out via transmission line 26 which may include a phone line, a cable modem, an ISD line, a cable or equivalent wireless data transmission system to transfer the data to server 30.

Figure 3A:
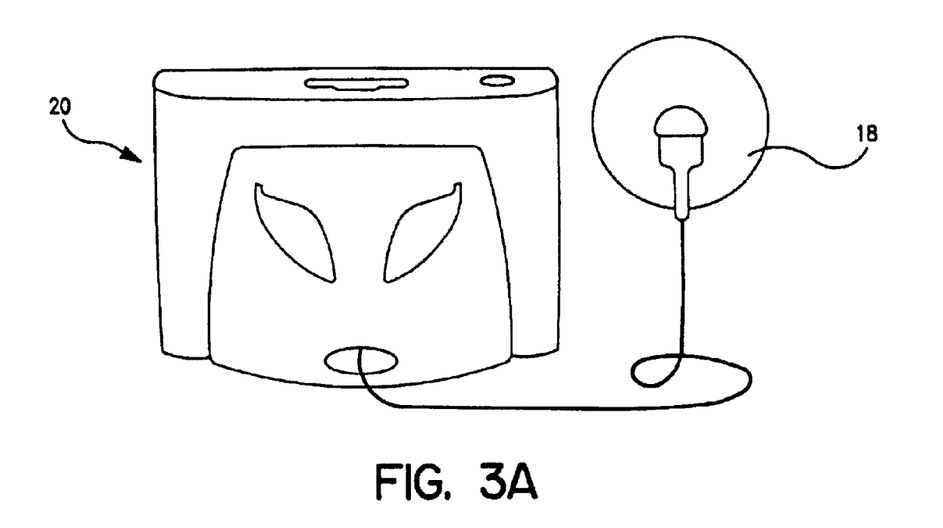
FIG. 3A is a perspective view of the IRM including a telemetry antenna.

Referring now to FIG. 3A, a perspective view of IRM 20 is shown with antenna 18, which antenna should be placed at the implant position to enable telemetry link in accordance with one embodiment of the present invention.

Figure 3B:
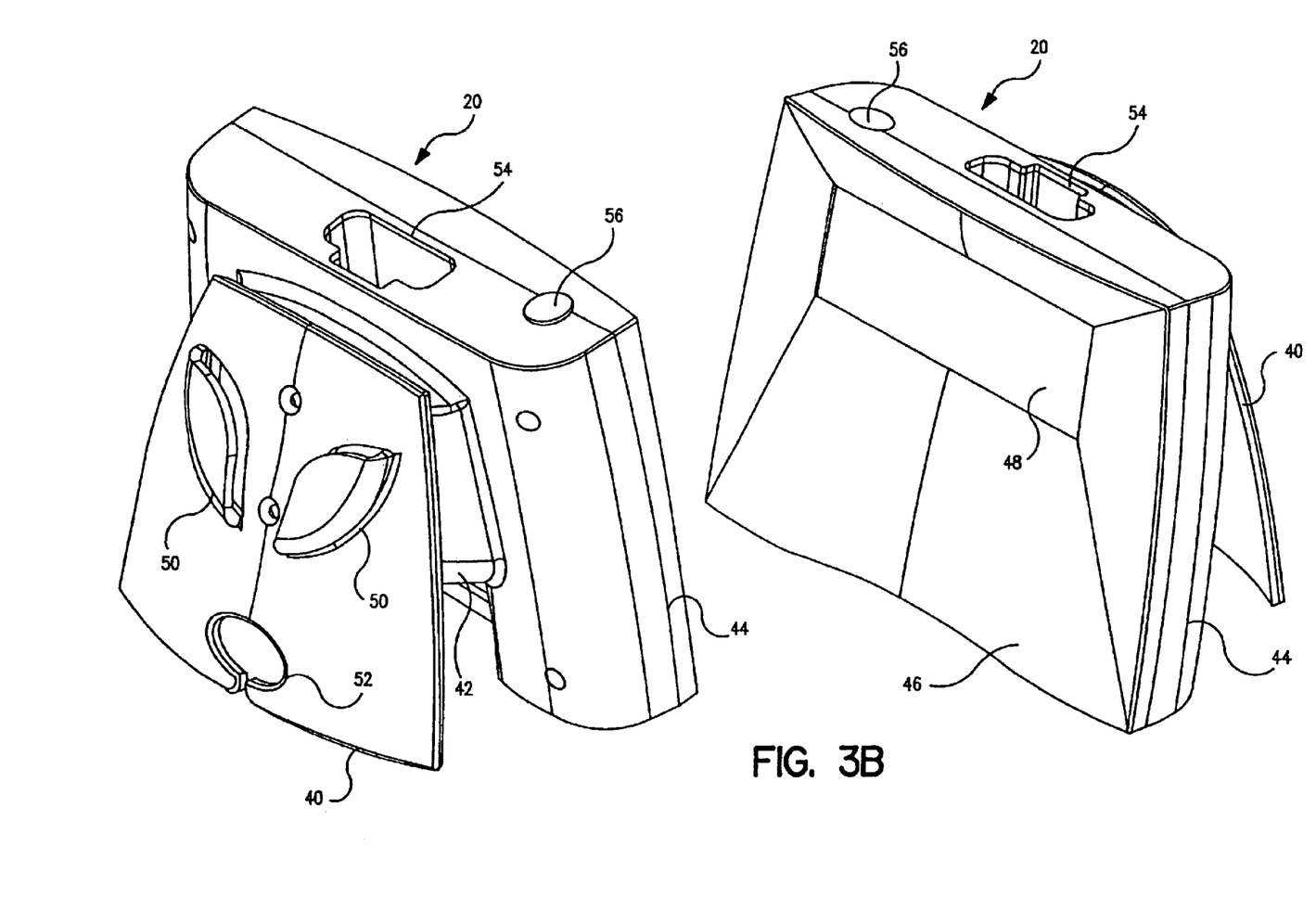
FIG. 3B is a perspective view of the IRM depicting the various front and back structures of the device.

FIG. 3B is a perspective drawing representing the various structures of IRM 20. Specifically, IRM 20 includes back panel 40 with support cradles attached externally thereof. Support cradles 50 enable to securely stow antenna 18 when not in use. Further, aperture 52 is designed to allow easy movement and access for cords and wires to connect to a panel behind back panel 40. Support structure 42 separates back panel 40 and front structure 44. In addition to providing stability to IRM 20, support structure 42 may be used to store the cord of antenna 18. Structure 44 represents the side panels that connect the back panels via support structure 42 to the front panel which includes panel 46 and interface panel 48. Top structure of IRM 20 includes slot 54 fitted for installing EPR 24 in position to download information into IRM 20. Button 56 is a push down start button that a patient or an operator needs to push in order to initiate the operations of IRM 20.

Figure 4A:
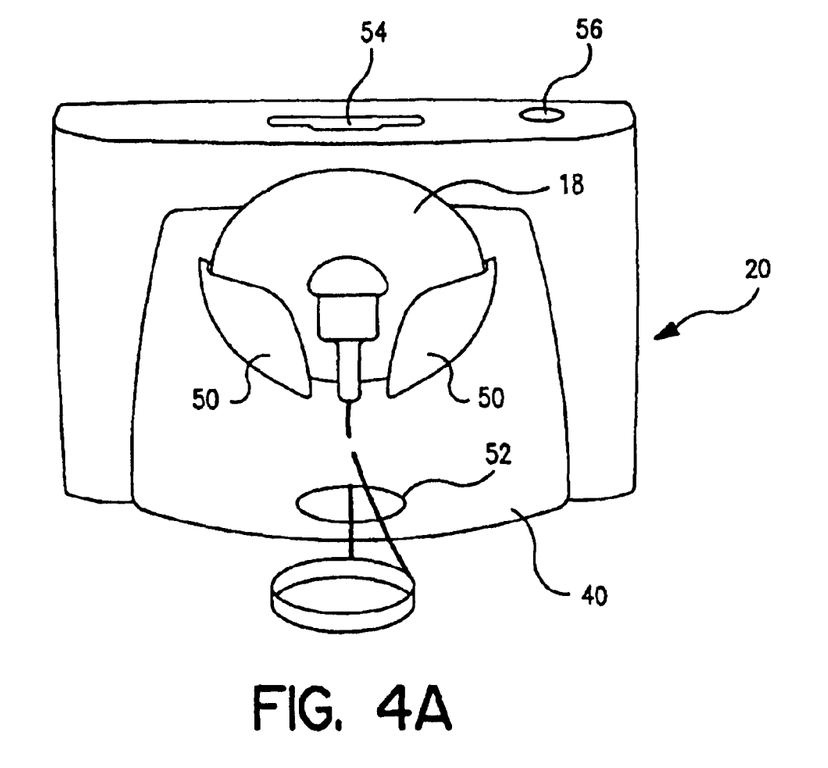
FIG. 4A is a perspective view representing the back side of the IRM with the antenna in a stored position.
Figure 4B:
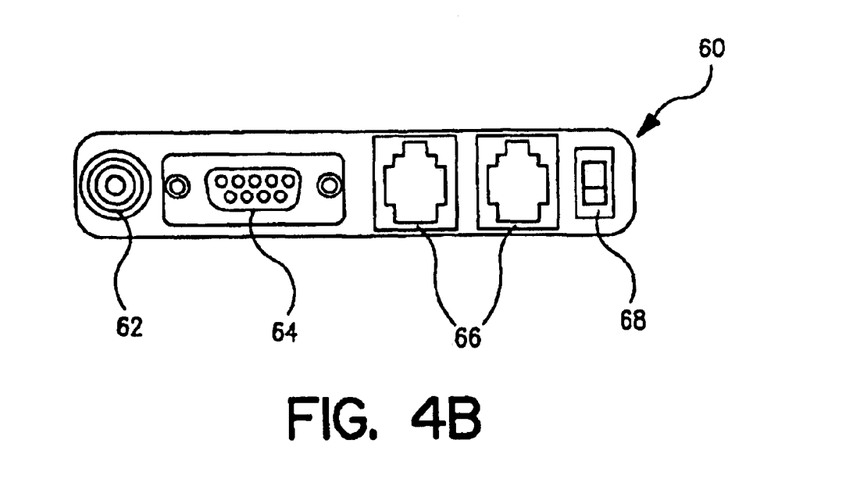
FIG. 4B is a front elevation view of the connection panel located behind the back panel of the IRM.

Referring now to FIGS. 4A and 4B, IRM 20 shown with antenna 18 in stowed position in support cradle 50. The power cord for antenna 18 is shown pulled through aperture 52 and disposed frontally at panel 40. FIG. 4B shows power panel 60 which is disposed behind panel 40. Power panel 60 includes power plug 62 to which a power cord could be attached to supply power to the IRM. Serial port 64 is implemented to connect the IRM 20 to PC 27, for example (See FIG. 1 or FIG. 2). Telephone connections 66 may be used to connect to a telephone jack and optionally a caller ID box in communication with an answering machine and a telephone. Dialing sequence switch 68 is placed in either a standard position which is up, or to dial a special number, down.

Figure 5A:
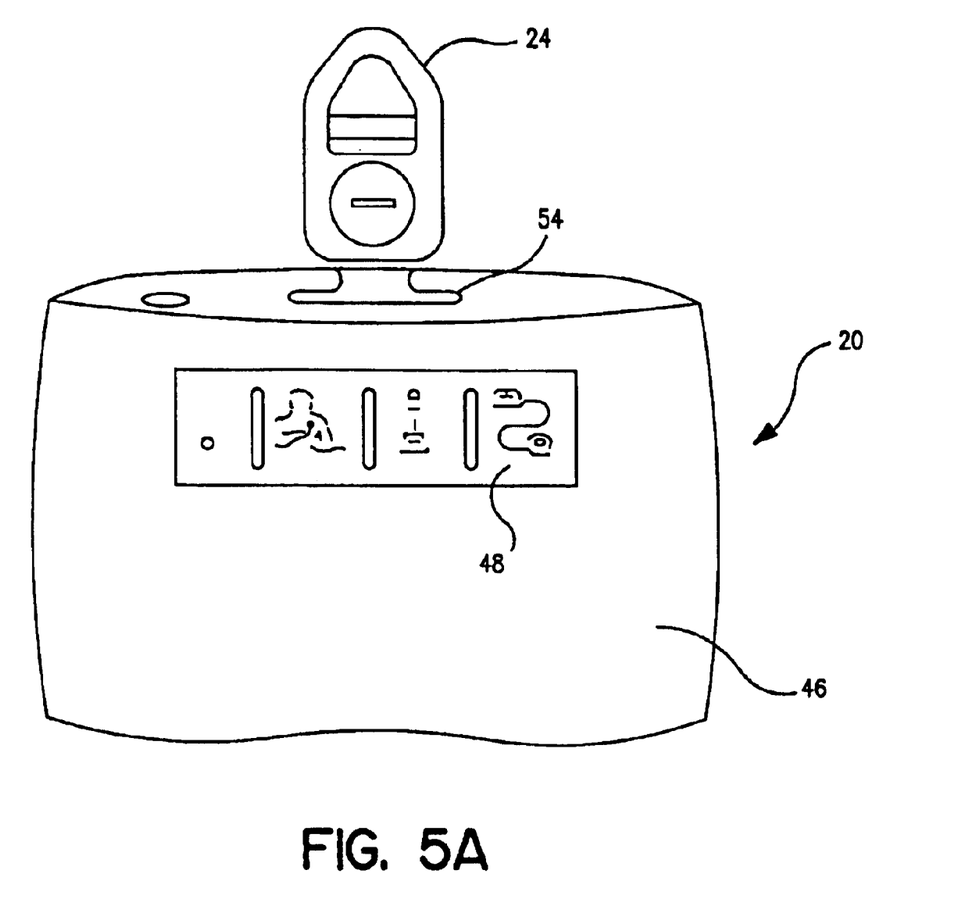
FIG. 5A is a representation of the engagement between the IRM and the external pressure reference (EPR).

FIG. 5A shows EPR 24 poised on top of slot 54 which it must engage to enable download of barometric pressure used for correlation to atmospheric pressure from EPR 24 to IRM 20.

Figure 5B:
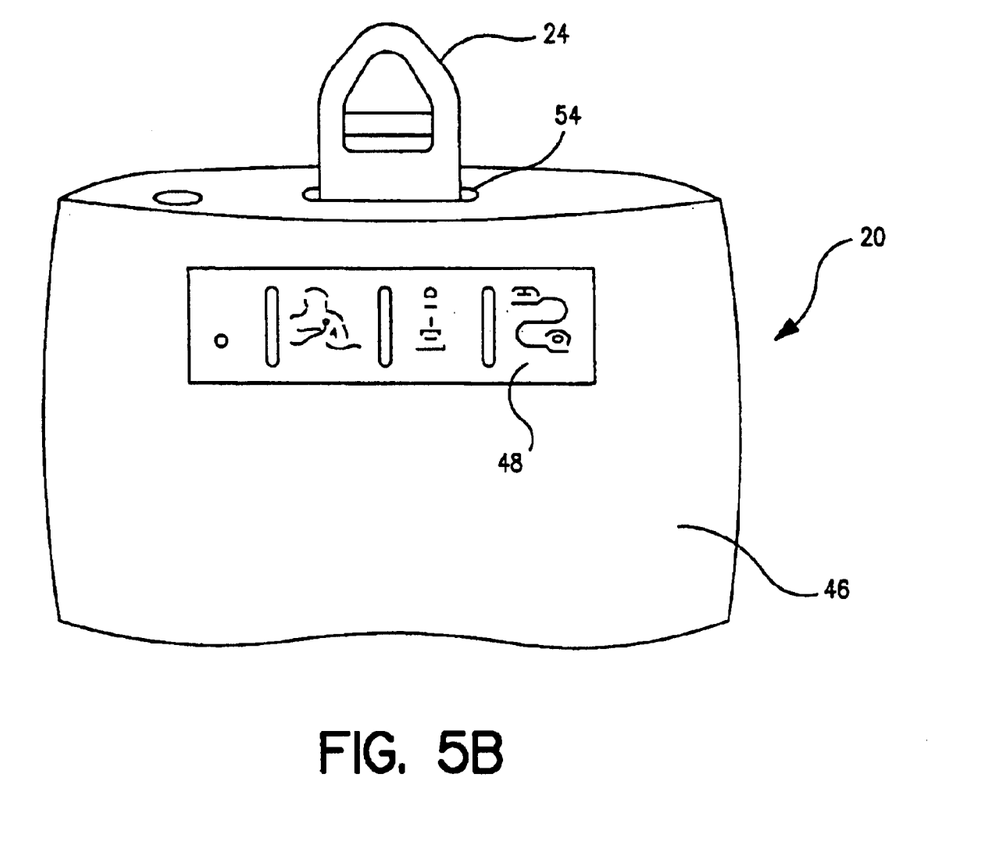
FIG. 5B represents the engagement of the EPR with the IRM.

FIG. 5B shows EPR 24 positioned/engaged in slot 54 to download barometric data into IRM 20.

Figure 6:
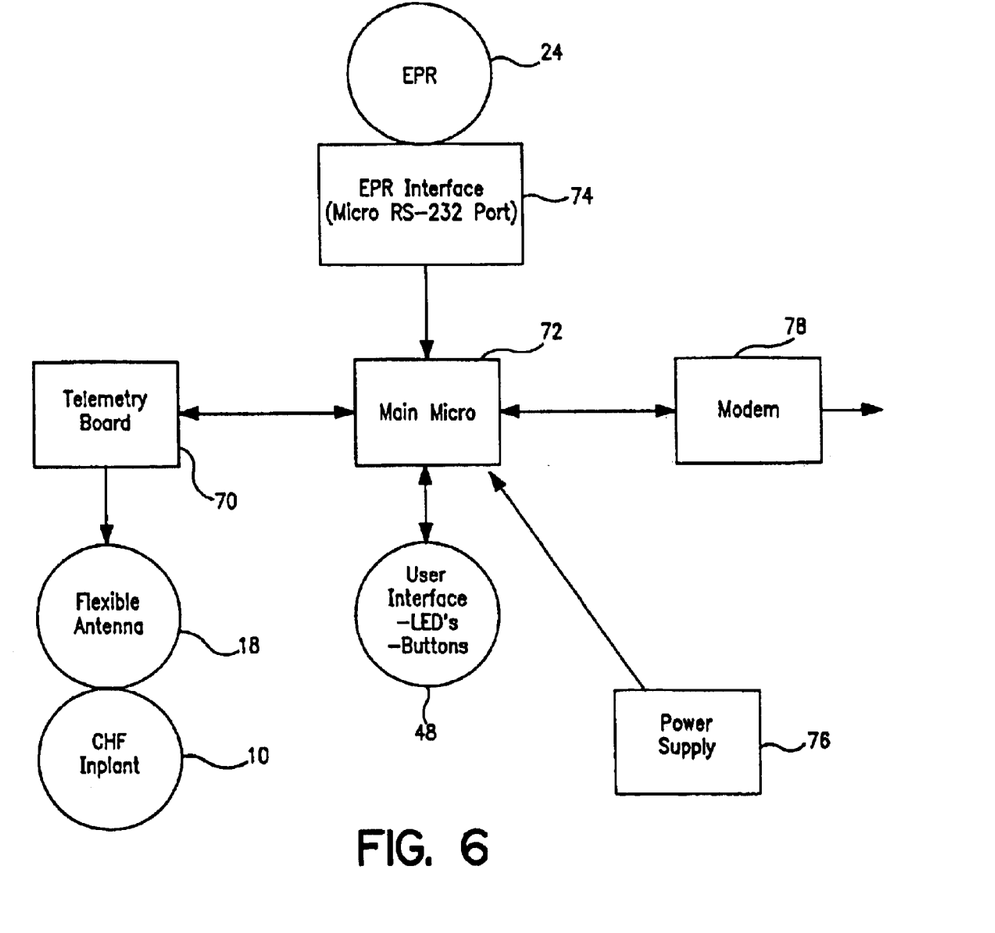
FIG. 6 is a block diagram representing the major components of the IRM and the EPR.

FIG. 6 is a block diagram representing the various components in accordance with the present invention. Specifically, main microcontroller 72 is an operable electric communication with EPR interface 74. EPR interface 74 is located in slots 54 to enable engagement between EPR 24 and IRM 20. Further, telemetry board 70 is in electrical communication with main microcontroller 72. In addition, telemetry board 70 is connected to flexible antenna 18. As discussed hereinabove, when antenna 18 is placed on implantable medical device such as Chronicle®, telemetry communication is established. Through this communication, data contained in IMD 10 is transferred to IRM 20. Further, main microcontroller 72 is connected to a power supply and modem 78 or equivalent. User interface LED buttons 48 operate via main microcontroller logic as will be discussed hereinbelow.

Figure 7:
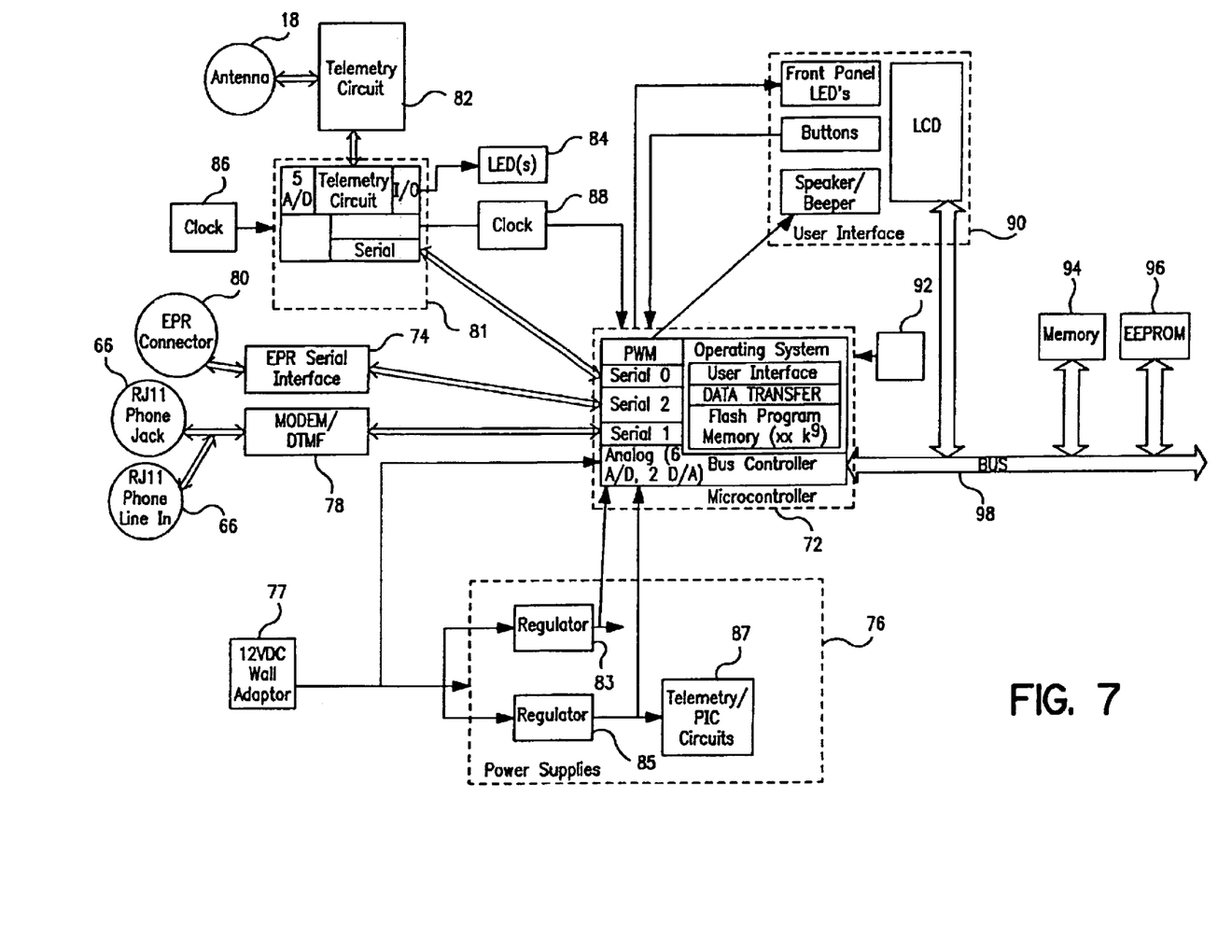
FIG. 7 is a simplified block/circuit diagram in accord with the preferred embodiment of the invention.

Reviewing microcontroller 72 in more detail in FIG. 7, EPR serial, interface 74 is in operable data communication with microcontroller 72 and EPR connector 80. It should be noted that EPR connector 80 is disposed in slots 54 (See FIG. 5A) to engage EPR 24. Microprocessor 81 is connected to telemetry circuit 82 which in turn is connected to antenna 18. Clocks 86 and 88 run various functions of microcontroller 81. Further, internal LED are represented by block 84.

Functionally, IRM 20 of the present invention could be used as an interface to transfer medical device information via the known wireless communication systems, patient data to remote location for review in chronic monitoring. IRM 20 operates in conjunction with EPR 24. EPR 24 is generally worn by the patient or kept in close proximity to monitor the barometric pressure of the environment.

In the preferred embodiment, IRM 20 is connected to a power outlet via connection 62. IRM 20 may also be connected to a telephone line via telephone connection 66, but this connection is not necessary for the IRM to work properly.

Assuming that IRM 20 is connected to a telephone line, a dialing sequence switch should be placed in the right setting. Most homes would use a standard sequence with switch 68 in an up position. When IRM 20 is connected to a power outlet, a green power light on interface panel 48 will come on. This green light is an indication that IRM 20 is on. EPR 24 is placed in slot 54 on top of IRM 20. The patient would then place antenna 18 over IMD 10. While holding antenna 18 over IMD 10, the patient would push start button 56 on top of IRM 20. Thereafter, a green LED will blink indicating that IRM 20 is gathering information from EPR 24 and IMD 10. When data transmission is complete the light will stop blinking and a second green light will come on. The second green light will start to blink when IRM 20 is transferring data to the remote station. Subsequently, when IRM 20 is done sending information, the second light will turn off and two or more beeps will sound. The patient then will remove EPR 24 from IRM 20 and wear it as a pager or keep it in the vicinity until it is time to use IRM 20 again.

The preceding specific embodiments are illustrative of the practice of the invention. It is to be understood, therefore, that other expedients known to those of skill in the art or disclosed herein may be employed without departing from the invention or the scope of the appended claims. It is therefore to be understood that within the scope of the appended claims, the invention may be practiced otherwise than as specifically described, without actually departing from the spirit and scope of the present invention.

What is claimed is:

1. A medical data transfer system comprising:
   a remote center;
   an implantable medical device having a hemodynamic monitor providing cardiac pressure data to the remote center;
   an information remote monitor operable to establish wireless communication with the implantable medical device to obtain cardiac pressure readings for a patient;
   an external pressure reference device operable to obtain external barometric pressure data correlated with patient cardiac pressure data obtained by said information remote monitor and adapted to be coupled to said information remote monitor to enable correction of cardiac pressure data;
   said information remote monitor, upon confirming that the external pressure reference device is coupled thereto operating to obtain implantable medical device cardiac pressure data, download external barometric pressure data from the external pressure reference device, initiate transmission over a communication link of cardiac pressure data and downloaded external barometric pressure data; and
   a communication link between the information remote monitor and the remote center.

2. The system of claim 1 further comprising a personal computer interfaced between the information remote monitor and the remote center.

3. The system of claim 1 wherein the communication link comprises a modem and a transmission medium.

4. The system of claim 1 wherein the implantable medical device executes high resolution data collection upon occurrence of a trigger event selected from a group consisting of a bradycardia trigger, a tachycardia trigger, and a patient activated trigger.

5. The system of claim 1 wherein wireless communication between the information remote monitor and the implantable medical device is bi-directional.

6. The system of claim 1 wherein the information remote monitor comprises a housing.

7. The system of claim 6 wherein the housing includes a slot for installation of the external pressure reference device during download of barometric pressure data.

8. The system of claim 6 wherein the housing comprises a detached antenna, a back panel having cradles to support the antenna in a stowed position, and a top structure having the installation slot for the external pressure reference device.

9. The system of claim 6 wherein the housing comprises a back panel having a power panel comprising a power cord attachment, a serial data port, and a telephone jack.

10. The system of claim 9 further comprising a dialing sequence switch.

11. The system of claim 6 wherein the housing comprises a front panel having a user interface panel comprising a power indicator, a first indicator of data download from the external pressure reference, and a second indicator of data transfer to the remote center.

12. The system of claim 1 wherein the information remote monitor simultaneously downloads data from the external pressure reference unit and data from the implantable medical device.

13. The system of claim 1 further comprising a personal computer connected to the information remote monitor to control the information remote monitor in programming the implantable medical device.

14. The system of claim 1 wherein the information remote monitor includes an internal modem to dial the remote center and transfer data over the communication link in a protocol selected from a group consisting of FTP, PPP and TCI/PIP protocols.

15. The system of claim 1 wherein the communication link comprises a transfer medium selected from a group consisting of a phone line, a cable modem, an ISD line, and a wireless data transmission system.

* * * * *

UNITED STATES PATENT AND TRADEMARK OFFICE
CERTIFICATE OF CORRECTION

PATENT NO. : 6,805,667 B2
APPLICATION NO. : 09/776265
DATED : October 19, 2004
INVENTOR(S) : Mark A. Christopherson et al.

It is certified that error appears in the above-identified patent and that said Letters Patent is hereby corrected as shown below:

Abstract, line 7, please delete "the IMO" and insert --the IMD--

Abstract, line 9, please delete "the IMO" and insert --the IMD--

Column 12, lines 4 and 5, please delete "and TCI/PIP" and insert --and TC/PIP--

Signed and Sealed this

First Day of April, 2008

JON W. DUDAS
*Director of the United States Patent and Trademark Office*